United States Patent [19]

Lu et al.

[11] Patent Number: 4,694,016

[45] Date of Patent: Sep. 15, 1987

[54] PHTHALAMIDE DERIVATIVES WITH ANTHELMINTIC ACTIVITY

[75] Inventors: Jing-Jong Lu; Herbert L. Wehrmeister, both of Terre Haute, Ind.

[73] Assignee: International Minerals & Chemical Corp., Terre Haute, Ind.

[21] Appl. No.: 788,935

[22] Filed: Oct. 18, 1985

[51] Int. Cl.$^4$ ..................... A61K 31/42; C07D 261/04
[52] U.S. Cl. ..................................... 514/380; 548/245
[58] Field of Search .......................... 548/245; 514/380

[56] References Cited

U.S. PATENT DOCUMENTS

| | | | |
|---|---|---|---|
| 3,879,532 | 4/1975 | Hass | 514/378 |
| 4,010,176 | 3/1977 | Kulsa | 514/378 |
| 4,062,861 | 12/1977 | Yukinaga | 514/380 |
| 4,275,214 | 6/1981 | Kelly | 548/243 |
| 4,322,429 | 3/1982 | Burow | 514/380 |
| 4,336,264 | 6/1982 | Wickiser | 514/380 |
| 4,593,024 | 6/1986 | Lu et al. | 514/234 |

FOREIGN PATENT DOCUMENTS 1590870  6/1981  United Kingdom .

OTHER PUBLICATIONS

D. G. Martin et al., "The Isolation, Structure, and Absolute Configuration of U-42,126 a Novel Antitumor Antibiotic," Tetrahedron Letters No. 27, pp. 2549-2552 (1973).

Silverman & Holladay, "Stereospecific Total Syntheses of the Natural Antitumor Agent (Alpha S,5S)-Alpha-Amino-3-Chloro-4,5-Dihydro-5-Isoxazoleacetic Acid and its Unnatural C-5 Epimer," Journal of the American Chemical Society, 103, pp. 7357-7358 (1981).

*Primary Examiner*—Donald G. Daus
*Assistant Examiner*—Barbara Cassatt
*Attorney, Agent, or Firm*—Wendell R. Guffey; Thomas L. Farquer

[57] ABSTRACT

Novel phthalamide compounds are disclosed having activity against a broad spectrum of parasitic worms and showing no toxicity to the host animal. These compounds are N-(3-chloro-4,5-dihydroisoxazol-4-yl)-N'-(substituted)phthalamides. A process for making these compounds and a method of administering them to animals are also disclosed.

4 Claims, No Drawings

PHTHALAMIDE DERIVATIVES WITH ANTHELMINTIC ACTIVITY

BACKGROUND OF THE INVENTION

Parasitic worms afflict mammals and fowl and thus pose an economic problem in the raising of cattle, swine, poultry and fur-bearing mammals. A significant number of compounds containing an amidine structural feature have shown significant anthelmintic activity, e.g., levamisole, albendazole, thiabendazole, morantel and bunamidine. However, a compound that is active against one type of worm is not necessarily active against other types. Likewise, toxicity often varies from one host animal to the next. Therefore there is a need for new agents with activities against a broad spectrum of endoparasitic worms and with low toxicity toward the host.

Numerous isoxazoles, isoxazolines and isoxazolidines have been isolated from natural sources or synthesized, and individual compounds or closely-related groups of compounds have been reported to be active as herbicides, or anti-protozoan drugs, or hypoglycemic agents, or anti-inflammatory agents or anti-pyretic agents. It is obvious that having activity against one particular pest or biological dysfunction does not mean a compound will also be active against parasitic worms. In addition, the activity of a compound even against a single pest is almost impossible to predict from its structure. For example, two structurally similar compounds can have dramatically different anthelmintic activities, one being very effective and the other totally ineffective.

SUMMARY OF THE INVENTION

It is an object of the invention to provide new compounds having anthelmintic activity.

It is an additional object of the present invention to provide new compounds having activity with low toxicity against gastrointestinal nematode infestations and cestode infestations in animals.

It is a further object of the invention to provide a process for synthesizing the new compounds.

It is another object of the invention to provide a method of treating mammals or fowl which are infested with parasitic worms or treating mammals or fowl to prevent infestation by parasitic worms.

In accordance with this invention there are provided anthelmintic compounds of the formula:

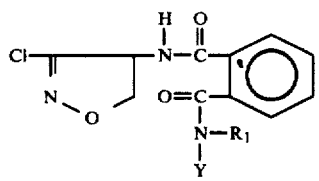

wherein $R_1$ is hydrogen, or methyl, and Y is aryl, arylalkyl, alkenyl, heteroarylalkyl, heteroarylheterocyclic, arylheterocyclic, or arylcycloalkyl group. Aryl groups, which include phenyl and naphthyl groups, may be substituted with nitro, alkyl, alkoxy or halo groups. Alkenyl groups generally contain from 2 to 20 carbon atoms, and may contain from 1 to 3 unsaturated bonds between adjacent carbon atoms. Heteroaromatic groups may be, for example, pyridyl, which may be substituted with a nitro group. Heterocyclic groups may include pyrrolidinyl, piperidinyl and piperazinyl groups. Cycloalkyl groups generally have 3 to 7 carbon atoms.

In another embodiment, this invention provides a method of treating animals with the claimed compounds. The invention also contemplates a method of making the claimed compounds.

The compounds of the present invention provide effective control of endoparasites. Moreover, they are relatively non-toxic to the host animals, thereby providing an obvious benefit in the husbandry of these animals.

DETAILED DESCRIPTION OF THE INVENTION

The isoxazoles of this invention have the formula

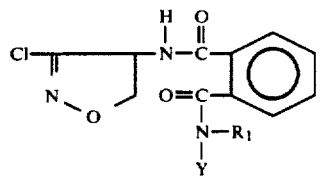

wherein $R_1$ is hydrogen, or methyl, and Y is aryl, arylalkyl, alkenyl, heteroarylalkyl, heteroarylheterocyclic, arylheterocyclic, or arylcycloalkyl group. Aryl groups, which include phenyl and naphthyl groups, may be substituted with nitro, alkyl, alkoxy or halo groups. Alkenyl groups generally contain from 2 to 20 carbon atoms, and may contain from 1 to 3 unsaturated bonds between adjacent carbon atoms. Heteroaryl groups may be, for example, pyridyl which may be substituted with a nitro group. Heterocyclic groups may include pyrrolidinyl, piperidinyl and piperazinyl groups, which may be substituted with a nitro group. Cycloalkyl groups generally have 3 to 7 carbon atoms.

Particularly preferred compounds of the present invention are N-(3-chloro-4,5-dihydroisoxazol-4-yl)-N'-phenylpropylphthalamide, N-(3-chloro-4,5-dihydroisoxazol-4-yl)-N'-4-bromobenzylphthalamide, and N-(3-chloro-4,5-dihydroisoxazol-4-yl)-N'-tolylethylphthalamide.

The compounds of this invention are active in controlling parasitic worms such as the hookworm *N. dubius*, the roundworm *N. brasiliensus*, the tapeworm *H. nana*, and the pinworms *S. obvelata* and *A. tetraptera*. Each of the compounds is effective against one or more of the worms but, as the examples demonstrate, each may not be effective against all species. Simple activity tests, within the skill of the art, can be employed to identify the spectrum of activity of any given compound.

Preparation of the compounds of this invention from D-cycloserine desirably is achieved by first protecting the active amino group by reacting D-cycloserine with a phthaloyl-containing compound to form a phthalimide with the 4-amino group of the D-cycloserine. One appropriate means is the use of N-carboethoxyphthalimide as the phthaloyl-containing compound as reported by Nefkens (Nature, 185, 309, 1960). This reaction can be carried out in the presence of sodium carbonate in aqueous solution at room temperature. Alternative methods of protecting the active amino group include using o-methoxycarbonylbenzoyl chloride as the phthaloyl-containing compound instead of N-carboethoxyphthalimide, as described by Hoogwater (Recueil de Travaux Chimiques de Peys-Bas, 92, 819–825, 1973), and via silylation followed by reaction with a phthaloyl chloride as described by Kume (Tetrahedron Letters, 23, 4365, 1981).

After the amino group has been protected, the ring system is modified by reaction with a phosphorous chloride. For example, the corresponding imidoyl chloride, 3-chloro-4-phthalimido-4,5-dihydroisoxazole can be formed by reaction with phosphorous oxychloride, as disclosed in J. Amer. Chem. Soc. 103, 942 (1981). Alternative methods of forming the imidoyl chloride include reaction with phosphorous pentachloride in refluxing nitromethane. This however is harsher than the method here employed, and tends to result in a lower yield of desired product and the formation of the undesired by-product 3-(3-keto-4-phthalimido-isoxazoline-2-yl)-4-phthalimido-isoxazoline.

The imidoyl chloride, 3-chloro-4-phthalimido-4,5-dihydroisoxazole, is a useful intermediate which can be used to make the compounds of this invention, as well as other compounds.

To form the compounds of the present invention, suitable amines such as, N-arylamines, N-arylalkylamines, N-alkenylamines, N-heteroarylalkylamines, N-heteroarylheterocycloamines, N-arylheterocycloamines, or N-arylcycloalkylamines are reacted in a suitable solvent, such as tetrahydrofuran with the intermediate imidoyl chloride, discussed above. Such reactions proceed readily at room temperature. Preferably, the amine is selected from the group consisting of benzylamine, p-methylbenzylamine, m-methylbenzylamine, p-methoxybenzylamine, alpha-methylbenzylamine, phenethylamine, p-tolylethylamine, N-methylphenylethylamine, beta-methylphenethylamine, beta-3,4-dimethoxy-phenylethylamine, phenylpropylamine, phenylbutylamine, fluorobenzylamine, 4-chlorobenzylamine, 4-bromobenzylamine, 2- and 3-pyridylmethylamines, 2- and 3-pyridylethylamines, piperonylamine, 4-(2-pyridyl)piperazinylamine, 4-phenylpiperazinylamine, 4-phenylpiperidinylamine, oleylamine, allylamine, 1-naphthalenemethylamine, phenylcyclopropylamine, and 3-fluorobenzylamine. Nucleophilic addition results in the formation of N-(3-chloro-4,5-dihydroisoxazol-4-yl)-N'-(substituted)-phthalamides.

The products can be isolated from the reaction medium by first concentrating the reaction mixture (e.g., in an evaporator) and then recrystallizing the compounds from a suitable solvent, such as ethyl acetate, or purifying by flash chromatography on silica gel and eluting with an appropriate solvent system, such as petroleum ether-ethyl acetate. Other methods of isolation will be apparent to those skilled in the art.

Parasitic worms afflict both mammals and birds, therefore the present invention is useful in the raising and husbandry of livestock such as cattle, swine, sheep and goats, domestic pets such as dogs and cats, rabbit, poultry such as turkeys, ducks, chickens and geese, and fur-bearing animals such as foxes, chinchilla and mink. The compounds of the present invention can be administered orally by conventional means and techniques known in the art. They can be used prophylactically to protect animals from infestation or therapeutically after the animals have been infested. In general, prophylactic dosages will be lower than those for pre-existing infestations. For example, dosages as low as 1 mg/kg of body weight may be sufficient to protect an animal from infestation by parasitic worms. Therapeutic dosages will often be from 10 to 100 times greater than prophylactic dosages.

The dosage used will depend on: (1) the animal to be treated; (2) which compound is to be used; (3) the infesting worms; and (4) the time and method of administration. Determination of the proper dosage in light of these variables is within the control and competence of one skilled in the art.

The chemotherapeutic agents of this invention can be administered in any of a variety of forms, alone or in combination, with other pharmaceuticals. They can be administered in a solid form or in liquid form in a suitable solvent. For example, they may be administered orally in admixture with an animal feed or fed separately as a supplement. Appropriate amounts of anthelmintic compound in the animal feed for therapeutic treatment of pre-existing infestations often are from about 300 ppm to about 2000 ppm.

Suitable dosages often are from about 0.5 to about 200 mg of active ingredient per kg of body weight of the host animal, depending on the particular compound, the infesting pest, the degree of infestation and the program of administering.

EXAMPLE 1

Phthaloylation of D-cycloserine with N-carboethoxyphthalimide

D-cycloserine (15.3 g, 0.15 mol) and sodium carbonate (15.9 g, 0.15 mol) were dissolved in 200 ml of water. N-carboethoxyphthalimide (36.0 g, 0.164 mol) was added to the solution and the mixture was stirred for 25 minutes and then filtered to remove unreacted N-carboethoxyphthalimide (12.1 g). The filtrate was chilled on ice bath and acidified with 4N HCl. Phthaloyl-D-cycloserine (18.5 g) precipitated out of solution and was collected by filtration, air dried, and recrystallized from ethyl acetate.

EXAMPLE 2

The synthesis of 3-chloro-4-phthalimido-4,5-dihydroisoxazole

The compound prepared in Example 1, phthaloyl-D-cycloserine (9.28 g, 40 mmol), was dissolved in 100 ml of nitromethane. Phosphorous oxychloride (4 ml, 43 mmol) was added to the solution, which was then heated to 100° C. in a two-hour period and kept at that temperature for an additional hour. The mixture was cooled to room temperature, and the solids were filtered off. The filtrate was concentrated, and the residue was extracted with ehtyl acetate. The solvent was removed and the product was purified by flash chromatography and eluted with 3:1 petroleum ether/ethyl acetate to yield 3-chloro-4-phthalimido-4,5-dihydroisoxazole (5.49 g).

EXAMPLE 3

The preparation of N-(3-chloro-4,5-dihydroisoxazol-4-yl)-N'-(benzyl)phthalamide

3-Chloro-4,5-phthalimido-4,5-dihydroisoxazole (2.5 g, 10 mmol) was dissolved in 100 ml of dried tetrahydrofuran. To the solution, 10 ml of benzylamine was added at room temperature. The reaction was stirred at room temperature for 4 hours, then concentrated in vacuo to remove solvent and excess benzylamine. Ethyl ether was added to the residue and insoluble solid was filtered off. The product was recrystallized from ethyl acetate to give 2.49 (69.6%) of the desired product.

EXAMPLE 4

The preparation of N-(3-chloro-4,5-dihydroisoxazol-4-yl)-N'-(p-methylbenzyl)phthalamide 3-Chloro-4-phthalimido-4,5-dihydroisoxazole (4 g, 16 mmol) was dissolved in 50 ml of dried tetrahydrofuran. 4-Methylbenzylamine (2.18 g, 18 mmol) was added at room temperature and the reaction solution was stirred at room temperature for 4 hours. The reaction mixture was concentrated in vacuo, and the residue recrystallized from chloroform to give 4.8 (80.7%) of the desired product.

EXAMPLE 5

The preparation of N-(3-chloro-4,5-dihydroisoxazol-4-yl)-N'-(m-methylbenzyl)phthalamide This reaction was performed as in example 2, except that the phenylalkylamine added was m-methylbenzylamine (1.94 g, 60 mmol) and the reaction was carried out for six hours. The reaction product was recrystallized from ethyl acetate giving 4.79, (80.5%) of the desired product.

EXAMPLES 6-17

Compounds 6-17 were synthesized from the compound of Example 2 in a manner analogous to the methods of examples 3, 4 and 5. Different conditions and reagents are as noted below.

| Example | ml of Tetrahydrofuran | mmole phenyl-alkyamine | Amine | Reaction Time | Recrystallized from | grams of product |
|---|---|---|---|---|---|---|
| 6 | 25 | 16 | p-methoxybenzylamine | 4 hr | ethyl acetate | 0.93 |
| 7 | 75 | 32 | alpha-methylbenzylamine | 4 days | ethyl acetate | 1.45 |
| 8 | 50 | 32 | phenethylamine | 4 hr | ethyl acetate | 4.4 |
| 9 | 50 | 28 | p-tolylethylamine | 4 hr | ethyl acetate | 4.28 |
| 10 | 50 | 17 | beta-methylphenethylamine | 18 hr | chloroform-hexane | 4.4 |
| 11 | 50 | 17 | beta-(3,4-dimethoxyphenyl) ethylamine | 4 hr | ethyl acetate | 5.9 |
| 12 | 50 | 17 | 3-phenyl-l-propylamine | 4 hr | ethyl acetate | 4.94 |
| 13 | 50 | 17 | 4-phenylbutylamine | 4 hr | ethyl acetate | 4.26 |
| 14 | 50 | 17 | p-fluorobenzylamine | 4 hr | ethyl acetate | 5.32 |
| 15 | 50 | 17 | p-chlorobenzylamine | overnight | ethyl acetate | 5.17 |
| 16 | 50 | 17 | N—methylphenethylamine | 3 days | flash chromotographed and eluted with 2:1, 1:1 petroleum ether/ethylacetate, ethyl acetate | 0.92 |
| 17 | 50 | 17 | 4-bromobenzylamine-HCl 50 triethylamine | 4 hr | ethyl acetate | 4.99 |

EXAMPLE 18

The compounds described above were administered to worm-infested mice in their diet, and the reductions in worm number were recorded. The results for the four worms against which the compounds were tested and showed good activity are tabulated in Table 2. The anthelmintic activity is based on reduction in worm burden and expressed as percent effectiveness.

No toxicity was observed in mice when these compounds were injected intraperitoneally (i.p.) at levels of 100 mg/kg of body weight or when fed at levels of 1,000 ppm in the diet.

TABLE 2

Anthelmintic Activity of N—(3-chloro-4,5-dihydroisoxazol-4-yl) - N'—(substituted) phthalmides

| Compound of Example No. | Dosage ppm in diet | % Reduction in the Number of Worms | | | |
|---|---|---|---|---|---|
| | | N. brasiliensis | H. nana | S. obvelata | A. tetraptera |
| 3 | 2000 | | 100 | 100 | 100 |
| | 1000 | | 100 | 98 | 100 |
| | 500 | | 0 | 100 | |
| | 300 | 46.5 | | | |
| 4 | 1000 | | 100 | 100 | 100 |
| | 500 | | 100 | 99 | 100 |
| | 300 | 63.8 | | | |
| 5 | 1000 | | 43 | 100 | 100 |
| | 500 | | 32 | 0 | 98 |
| | 300 | 55.7 | | | |
| 6 | 1000 | | 64 | 68 | 63 |
| | 500 | | 100 | 0 | 100 |
| | 300 | 48.0 | | | |
| 7 | 1000 | | 74 | 43 | 66 |
| | 500 | | 0 | 31 | 82 |
| | 300 | 45.7 | | | |
| 8 | 1000 | | 100 | 98 | 100 |

TABLE 2-continued

Anthelmintic Activity of
N—(3-chloro-4,5-dihydroisoxazol-4-yl) - N'—(substituted) phthalmides

| Compound of Example No. | Dosage ppm in diet | % Reduction in the Number of Worms | | | |
|---|---|---|---|---|---|
| | | N. brasiliensis | H. nana | S. obvelata | A. tetraptera |
|  | 500 |  | 100 | 29 | 100 |
|  | 300 | 44.2 |  |  |  |
| 9 | 1000 |  | 100 | 67 | 100 |
|  | 500 |  | 100 | 0 | 100 |
|  | 300 | 50.6 |  |  |  |
| 10 | 1000 |  | 100 | 0 | 100 |
|  | 500 |  | 100 | 0 | 100 |
|  | 300 | 25 |  |  |  |
| 11 | 1000 |  | 100 | 0 | 100 |
|  | 500 |  | 100 | 0 | 100 |
|  | 300 | 30.6 |  |  |  |
| 12 | 1000 |  | 100 | 100 | 100 |
|  | 500 |  | 100 | 91 | 100 |
|  | 300 | 68 |  |  |  |
| 13 | 1000 |  | 100 | 100 | 100 |
|  | 500 |  | 100 | 0 | 90 |
|  | 300 | 39.2 |  |  |  |
| 14 | 100 |  | 100 | 0 | 100 |
|  | 500 |  | 0 | 0 | 100 |
|  | 300 | 25 |  |  |  |
| 15 | 1000 |  | 100 | 100 | 100 |
|  | 500 |  | 0 | 0 | 96 |
|  | 300 | 25 |  |  |  |
| 16 | 1000 |  | 100 | 100 | 100 |
|  | 500 |  | 100 | 47 | 47 |
|  | 300 | 44.5 |  |  |  |
| 17 | 1000 |  | 100 | 100 | 100 |
|  | 500 |  | 0 | 0 | 96 |
|  | 300 | 46.9 |  |  |  |

At 2,000 ppm N—(3-chloro-4,5-dihydroisoxazol-4-yl)-N'—(benzyl)phthalamide shows activity against the hookworm N. dubius, in being able to reduce the size of the worm.

EXAMPLES 19-31

The following compounds were synthesized in analogous reactions to those discussed above in Examples 3-18 using the corresponding amine as a reagent. Each was tested against the worms H. nana and N. dubius at a dosage of 1,000 ppm using the procedure described in Example 18.

Although none of these compounds proved effective in reducing the number of N. dubius, the compound of Example No. 30 had the effect of stunting N. dubius.

| Compound of Example No. | N—(3-chloro-4,5-dihydro-isoxazol-4-yl)-N'—(substituted) phthalamide | % Reduction in No. of H. nana |
|---|---|---|
| 19 | 3-pyridylmethyl | 100 |
| 20 | 4-pyridylethyl | 100 |
| 21 | 2-pyridylethyl | 100 |
| 22 | 2-pyridylmethyl | 100 |
| 23 | 4-nitro-2-pyridylamino-ethyl | 100 |
| 24 | piperonyl | 100 |
| 25 | 4-phenylpiperazinyl | 100 |
| 26 | 4-phenylpiperidinyl | 100 |
| 27 | oleyl | 72 |
| 28 | allyl | 100 |
| 29 | 1-naphthalenemethyl | 100 |
| 30 | trans-phenylcyclopropyl | 100 |
| 31 | m-fluorobenzyl | 77 |

What is claimed is:

1. An anthelmintic compound selected from the group consisting of N-(3-chloro-4,5-dihydro-isoxazol-4-yl)-N'-(m-methylbenzyl)phthalamide, N-(3-chloro-4,5-dihydro-isoxazol-4-yl)-N'-(p-tolylethyl)phthalamide, and N-(3-chloro-4,5-dihydro-isoxazol-4-yl)-N'-(3-phenyl-1-propyl)phthalamide.

2. A method for prophylactically or therapeutically treating mammals and fowl to combat parasitic worm infestations which comprises orally administering to said mammals and fowl an effective amount of a compound selected from the group consisting of N-(3-chloro-4,5-dihydro-isoxazol-4-yl)-N'-(m-methylbenzyl)phthalamide, N-(3-chloro-4,5-dihydro-isoxazol-4-yl)-N'-(p-tolylethyl)phthalamide, and N-(3-chloro-4,5-dihydro-isoxazol-4-yl)-N'-(3-phenyl-1-propyl)phthalamide.

3. The method of claim 2 wherein said compound is administered in admixture with feed in an amount of from about 300 to about 2,000 ppm of the feed.

4. The method of claim 2 wherein said compound is administered in a dosage of from about 0.5 to about 200 mg of active ingredient per kg of animal body weight.

* * * * *

UNITED STATES PATENT AND TRADEMARK OFFICE
CERTIFICATE OF CORRECTION

PATENT NO. : 4,694,016

DATED : September 15, 1987

INVENTOR(S) : Jing-Jong Lu et al.

It is certified that error appears in the above-identified patent and that said Letters Patent are hereby corrected as shown below:

Column 3, line 37, "3-pyridylethylamines" should read
-- 4-pyridylethylamines --

Column 4, line 49, "ehtyl" should read -- ethyl --

Column 6, Table 1, column 6, line 15, "chromotographed" should read
-- chromatographed --

Column 6, Table 2, in the Heading, line 3, "phthalmides" should read
-- phthalamides --

Column 6, Table 2, column 5, line 3, "100" should read -- 0 --

Column 6, Table 2, column 6, line 3, insert -- 100 --

Signed and Sealed this

Twenty-first Day of June, 1988

*Attest:*

DONALD J. QUIGG

*Attesting Officer*     *Commissioner of Patents and Trademarks*